US012731698B2

(12) United States Patent
Samudrala et al.

(10) Patent No.: US 12,731,698 B2
(45) Date of Patent: Sep. 8, 2026

(54) SYSTEM AND METHOD OF PROVIDING EMERGENCY NOTIFICATIONS ACROSS AN AD-HOC NETWORK IN A HEALTH CARE FACILITY

(71) Applicant: CarePredict, Inc., Plantation, FL (US)

(72) Inventors: Srinaag V. Samudrala, Pompano Beach, FL (US); Christopher Crocker, Plantation, FL (US)

(73) Assignee: CarePredict, Inc., Plantation, FL (US)

( * ) Notice: Subject to any disclaimer, the term of this patent is extended or adjusted under 35 U.S.C. 154(b) by 300 days.

(21) Appl. No.: 18/411,579

(22) Filed: Jan. 12, 2024

(65) Prior Publication Data

US 2025/0210208 A1 Jun. 26, 2025

Related U.S. Application Data

(60) Provisional application No. 63/613,389, filed on Dec. 21, 2023.

(51) Int. Cl.

| | |
|---|---|
| ***G16H 80/00*** | (2018.01) |
| ***H04W 4/12*** | (2009.01) |
| ***H04W 4/90*** | (2018.01) |
| ***H04W 84/18*** | (2009.01) |

(52) U.S. Cl.
CPC .............. *G16H 80/00* (2018.01); *H04W 4/12* (2013.01); *H04W 4/90* (2018.02); *H04W 84/18* (2013.01)

(58) Field of Classification Search
CPC .......... G16H 80/00; H04W 4/12; H04W 4/90; H04W 84/18; H04W 4/80; G01S 5/0273; G01S 5/0278; G01S 2205/02; G01S 2205/09; G08B 21/00; G08B 21/0453; G08B 21/0263
See application file for complete search history.

(56) References Cited

U.S. PATENT DOCUMENTS

| | | | | |
|---|---|---|---|---|
| 11,323,196 B1 * | 5/2022 | Newton | H04B 7/0417 |
| 2013/0143535 A1 * | 6/2013 | Leppanen | H04W 4/80 455/414.1 |
| 2014/0195257 A1 * | 7/2014 | Perkins | G16H 40/20 705/2 |
| 2015/0112162 A1 | 4/2015 | Wilmink | |
| 2015/0112163 A1 | 4/2015 | Wilmink | |
| 2015/0257096 A1 * | 9/2015 | Lee | H04L 12/189 370/311 |
| 2017/0084151 A1 * | 3/2017 | Beaty | G08B 21/0227 |

(Continued)

*Primary Examiner* — Davetta W Goins
(74) *Attorney, Agent, or Firm* — DLA Piper LLP (US)

(57) ABSTRACT

A system and method of transmitting an emergency notification among patients in a health care facility is disclosed herein. The first patient device establishes an ad-hoc network of devices within the health care facility. The ad-hoc network of devices includes a plurality of other patient devices and a plurality of health care provider devices. The first patient device detects a trigger event for sending a message across the ad-hoc network. Responsive to the detecting, the first patient device generates the message that includes a header that includes a unique identifier corresponding to the first patient device, a locally stored list of neighboring devices to the first patient device, and an indication of the trigger event. The first patient device causes the message to propagate across the ad-hoc network by broadcasting the message via a radio transceiver of the first patient device.

18 Claims, 5 Drawing Sheets

(56) References Cited

U.S. PATENT DOCUMENTS

| | | | | |
|---|---|---|---|---|
| 2017/0293729 | A1 | 10/2017 | Movva | |
| 2018/0027070 | A1* | 1/2018 | Jhanji | H04W 4/80<br>709/217 |
| 2019/0239775 | A1 | 8/2019 | Movva et al. | |
| 2020/0153785 | A1* | 5/2020 | Fulton | H04W 12/102 |
| 2021/0290184 | A1* | 9/2021 | Ahmed | A61B 5/0008 |
| 2023/0333201 | A1* | 10/2023 | Regani | G01S 13/86 |

* cited by examiner

400
Storage Device
Serv. 1
Serv. 2
Serv. 3
430
432
434
436
405
Memory 415
ROM
RAM
420
425
Processor
410
Cache
412
Input Device
445
Output Device
435
Communication Interface
440

450
Communication Interface
490
RAM
475
Storage Device
470
Processor
455
Chipset
460
Output
465
Bridge
480
User Interface Components
485

SYSTEM AND METHOD OF PROVIDING EMERGENCY NOTIFICATIONS ACROSS AN AD-HOC NETWORK IN A HEALTH CARE FACILITY

TECHNICAL FIELD

Embodiments disclosed herein generally relate to systems and methods for sending emergency notifications in an ad-hoc network of devices in a health care facility.

BACKGROUND

Wearables are ubiquitous now in personal health. Wearables typically include sensors that include accelerometers, gyros, inclinometers, and magnetometers, among others. Such sensors can detect certain trigger events, such as location-based trigger events, or activities, such as walking, running, sleeping, sitting, falling, and rolling among other functional states of a wearer. In the context of a health care facility, wearables play a vital role in managing patient health and safety.

SUMMARY

In some embodiments, a method of transmitting an emergency notification among patients in a health care facility is disclosed herein. The first patient device establishes an ad-hoc network of devices within the health care facility. The ad-hoc network of devices includes a plurality of other patient devices and a plurality of health care provider devices. The first patient device detects a trigger event for sending a message across the ad-hoc network. Responsive to the detecting, the first patient device generates the message that includes a header that includes a unique identifier corresponding to the first patient device, a locally stored list of neighboring devices to the first patient device, and an indication of the trigger event. The first patient device causes the message to propagate across the ad-hoc network by broadcasting the message via a radio transceiver of the first patient device.

In some embodiments, a health care system for a health care facility. The health care system includes a first patient device. The first patient device includes a processor and a memory. The memory has programming instructions stored thereon, which, when executed by the processor, cause the first patient device to perform operations. The operations include establishing, by the first patient device, an ad-hoc network of devices within the health care facility. The ad-hoc network of devices includes a plurality of other patient devices and a plurality of health care provider devices. The operations further include detecting, by the first patient device, a trigger event for sending a message across the ad-hoc network. The operations further include, responsive to the detecting, generating, by the first patient device, the message that includes a header that includes a unique identifier corresponding to the first patient device, a locally stored list of neighboring devices to the first patient device, and an indication of the trigger event. The operations further include causing, by the first patient device, the message to propagate across the ad-hoc network by broadcasting the message via a radio transceiver of the first patient device.

In some embodiments, a non-transitory computer readable medium is disclosed herein. The non-transitory computer readable medium includes one or more sequences of instructions, which, when executed by a processor, causes a first patient device to perform operations. The operations include establishing, by the first patient device, an ad-hoc network of devices within the health care facility. The ad-hoc network of devices includes a plurality of other patient devices and a plurality of health care provider devices. The operations further include detecting, by the first patient device, a trigger event for sending a message across the ad-hoc network. The operations further include, responsive to the detecting, generating, by the first patient device, the message that includes a header that includes a unique identifier corresponding to the first patient device, a locally stored list of neighboring devices to the first patient device, and an indication of the trigger event. The operations further include causing, by the first patient device, the message to propagate across the ad-hoc network by broadcasting the message via a radio transceiver of the first patient device.

BRIEF DESCRIPTION OF THE FIGURES

The accompanying drawings, which are incorporated herein and form part of the specification, illustrate the present disclosure and, together with the description, further serve to explain the principles of the present disclosure and to enable a person skilled in the relevant art(s) to make and use embodiments described herein.

Figure 1:
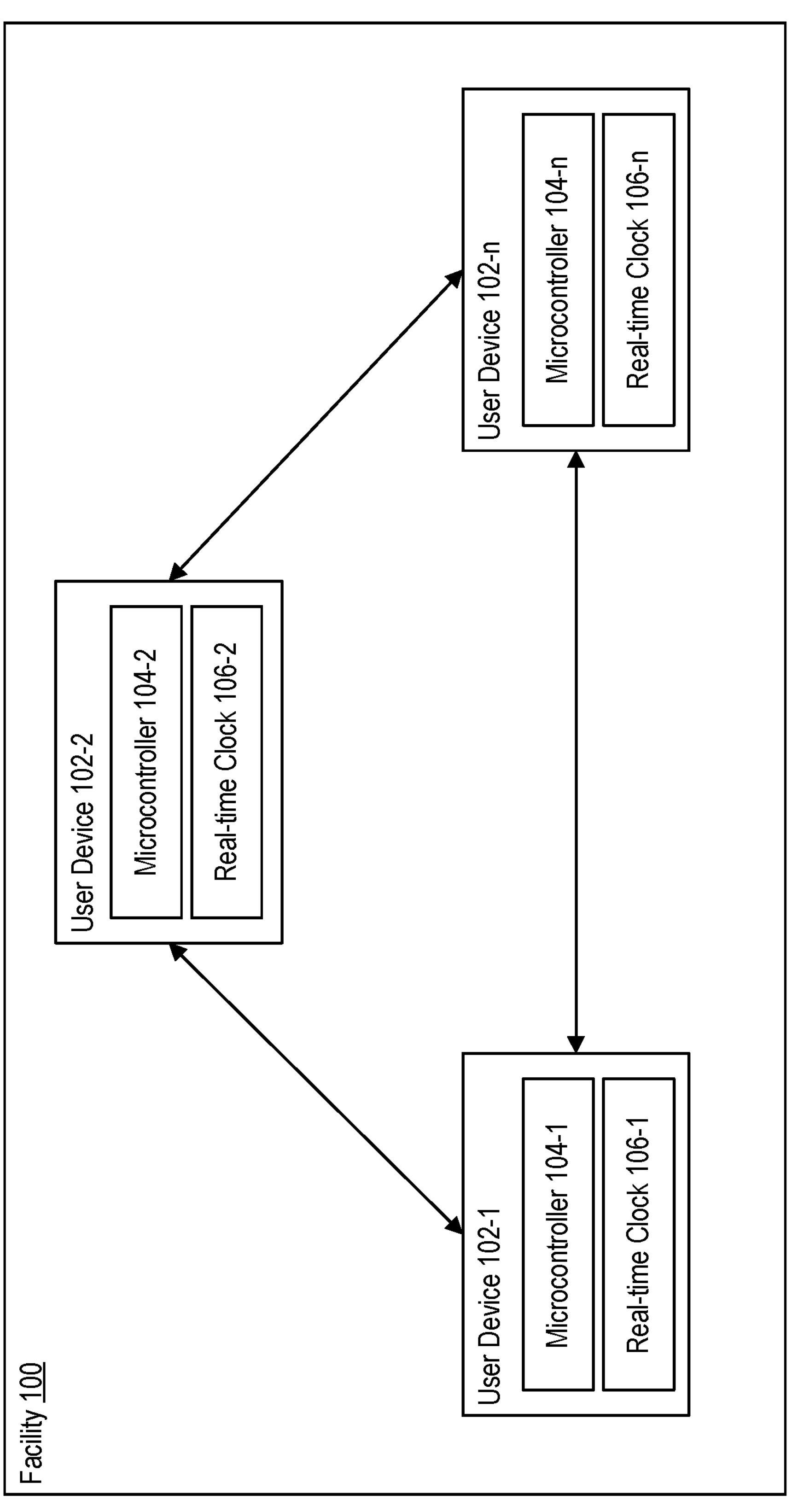
FIG. 1 is a block diagram illustrating an exemplary health care facility, according to example embodiments of the present disclosure.

The features of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. Additionally, generally, the left-most digit(s) of a reference number identifies the drawing in which the reference number first appears. Unless otherwise indicated, the drawings provided throughout the disclosure should not be interpreted as to-scale drawings.

DETAILED DESCRIPTION

As a person ages, they typically require an increased level of attention for their well-being. Often times, aging persons are placed in senior health care facilities where they can receive round the clock care. Such senior health care facilities may employ various systems to make sure their residents receive the care they need.

One critical issue that arises in such health care facilities is when their resident management system over relies on wireless connectivity and/or power to operate. For example, in the case of an Internet outage or a power outage, these systems will be ineffective in delivering the required assistance to the residents.

Currently, there are several conventional approaches that provide alternative communication paths outside of the Internet/Wi-Fi context. One such approach is the creation of a mesh network among participant devices within a health care facility. While useful, mesh networks are reliant on a power source to maintain its nodes in an active or running state.

Another conventional approach involves device-to-device mesh networks. Device-to-device mesh networks require that there be a root node through which all traffic must run. As those skilled in the art understand, there is an inherent limitation in device-to-device mesh networks in that when the devices are mobile, such as in the case of a health care facility, any device-including the root node—can drop out unexpectedly. When such issue arises, the entire network is required to re-initiate a node selection process, thus requiring additional downtime and causing a further drain on battery powered devices.

Another conventional approach involves device-to-device communication, outside of the mesh network context. Device-to-device communication is limited by its communication range. For example, most Internet-of-things (IoT) devices use low power radio antennas to communicate directly with other devices. As those skilled in the art understand, low power radio antennas have a relatively short communication range. Thus, when implementing low power radio antennas across a large facility, such as a healthcare facility, it is very likely that there will be communication issues among participant devices due to the short range communication limitation.

To improve upon conventional systems, one or more techniques described herein provide a decentralized communication network within a healthcare facility that is able to operate on limited battery power and no longer rely on a consistent organized structure of devices. For example, one or more techniques disclosed herein employ a radio relay system within a health care facility to improve upon conventional techniques. By utilizing a radio relay system, devices within the health care facility can communicate across greater distances compared to conventional device-to-device communication protocols, without the need for a centralized root node such as that required in conventional mesh networks. Further, by utilizing a radio relay system, the present approach reduces the power consumption of devices within the health care facility, thus ensuring that when there is a power outage or Internet outage important communications can be communicated across devices.

FIG. 1 is a block diagram illustrating an example health care facility 100, according to example embodiments. As shown, health care facility 100 may include a plurality of user devices 102 (e.g., user device 102-1, user device 102-2, and user device 102-*n*). User devices 102 may form an ad-hoc network within health care facility 100 by communicating directly or indirectly with other devices. In other words, user devices 102 may form a decentralized or ad-hoc network within health care facility 100.

User device 102 may be operated by a user. In some embodiments, user device 102 may be operated by a patient or resident of health care facility 100. In some embodiments, user device 102 may be operated by a care provided of health care facility 100. User device 102 may be representative of a wearable device, mobile device, a tablet, a desktop computer, or any computing system having the capabilities described herein.

In some embodiments, user device 102 may be representative of a wearable sensor device that is configured to monitor patients around health care facility 100. In some embodiments, user device 102 may be representative of a wearable sensor device configured to track a patient's location with health care facility 100, determine whether the patient has fallen, determine whether a patient is running, sleeping, sitting, and the like. For example, wearable sensor device may be configured to perform any of the functionality described in U.S. patent application Ser. No. 15/891,107, U.S. patent application Ser. No. 13/896,306, U.S. patent application Ser. No. 14/057,687, and U.S. patent application Ser. No. 14/057,676, which are hereby incorporated by reference in their entries.

More generally, user device 102 may be representative of any user device that includes a microcontroller and real-time clock. For example, as shown, health care facility 100 includes user device 102-1, user device 102-2, and user device 102-*n* (generally "user device 102"). Each user device 102 may include a microcontroller 104 and a real-time clock 106. For example, as shown, user device 102-1 includes microcontroller 104-1 and real-time clock 106-1; user device 102-2 includes microcontroller 104-2 and real-time clock 106-2; and user device 102-*n* includes microcontroller 104-*n* and real-time clock 106-*n*. For ease of discussion, microcontroller 104-1, 104-2, and 104-*n* may be referred to generally as microcontroller 104. Similarly, real-time clock 106-1, 106-2, and 106-*n* may be referred to generally as real-time clock 106.

Microcontroller 104 may be configured to control one or more operations performed by user device 102. For example, microcontroller 104 may include a radio transceiver configured to transmit data, receive data, and process data. Using a specific example, microcontroller 104, via its transceiver, may be configured to transmit a message or notification to another device, receive a message or notification from another device, and/or process any received messages. In some embodiments, microcontroller 104 may be dedicated solely to message and notification handling. In some embodiments, microcontroller 104 may be configured to control all operations performed by user device 102, such as those described in U.S. patent application Ser. No. 15/891,107, U.S. patent application Ser. No. 13/896,306, U.S. patent application Ser. No. 14/057,687, and U.S. patent application Ser. No. 14/057,676, which are hereby incorporated by reference in their entries.

In some embodiments, microcontroller 104 may facilitate creation of an ad-hoc network among user device 102 in health care facility 100. For example, microcontroller 104 may be configured to execute a neighbor discovery process using a neighbor selection algorithm. During the neighbor discovery process, each user device 102 may generate and send a neighbor discovery packet in a single broadcast message that is sent by every device in the network at a scheduled time based on synced high accuracy real time clock. During the neighbor discovery process, every user device 102 in health care facility 100 may learn who its neighbors are and how far their neighbors are to each other based on received signal strength indicators (RSSIs) of the received discovery packets. In some embodiments, multiple discovery packets may be sent from each device in fixed time intervals over the course of the discovery period. Multiple discovery packets may be utilized to ensure that the system is resilient to any clock drifting.

In some embodiments, neighbor selection may occur based on the perceived distance between two user devices 102 as determined by an RSSI in the discovery packet. For example, a given user device 102 (e.g., user device 102-1) may select another user device 102 (e.g., user device 102-2) as a neighbor device based on its RSSI exceeding a threshold level; user device 102-1 may not select user device 102-*n* as a neighbor based on its RSSI not exceeding the threshold level. In some embodiments, the criteria for a given user device 102 to select neighbor devices may change based on various success metrics of a given transmission of a message through the network. In some embodiments, the neighbor selection algorithm may decide which user devices should be neighbors based on the reach of a discovery message through the ad-hoc network.

In some embodiments, each discovery packet that is generated may include a time that real-time clock 106 carries. For example, real-time clock 106 may facilitate synchronization of user devices 102 within the ad-hoc network. Each real-time clock 106 may maintain a time local to its user device 102. To ensure that all user devices 102 wake up asynchronously, the ad-hoc network may leverage real-time clocks 106. During the discovery process, each discovery message or packet may include a time that a corresponding real-time clock 106 carries. For example, as user device 102 selects neighbors, user device 102 effectively synchronizes its real-time clock 106 with the real-time clocks of its neighbors to ensure clock synchronization in the case of a prolonged Wi-Fi or power outage.

After the discovery process is complete and the neighbors have been identified, messages can be sent through the ad-hoc network. In operation, a first user device (e.g., user device 102-1) may send a message to each of its neighbors. For example, assume that user device 102-1 is a neighbor of user device 102-2 and user device 102-*n*; similarly, assume that user device 102-2 is a neighbor of user device 102-*n* and another user device (e.g., user device 102-*m*). When user device 102-1 sends a message, user device 102-1 may send it to every neighbor on its list. The message generated by user device 102-1 may include all of its neighbors. When, for example, user device 102-2 receives the message, before relaying the message to its neighbors, user device 102-2 may check the list of neighbors included in the message to filter out common neighbors. For example, user device 102-2 may determine that the message was also sent to user device 102-*n*, which is also a neighbor to user device 102-2. Thus, when user device 102-2 relays the message to its neighbors, user device 102-2 may only send the message to the non-overlapping neighbors, i.e., user device 102-*m*.

In some embodiments, all receiving user devices may also maintain a circular buffer of sent or relayed messages to filter out duplicate messages. Such approach may ensure maximum message propagation through the network with high efficiency and minimal redundant transmissions.

Figure 2:
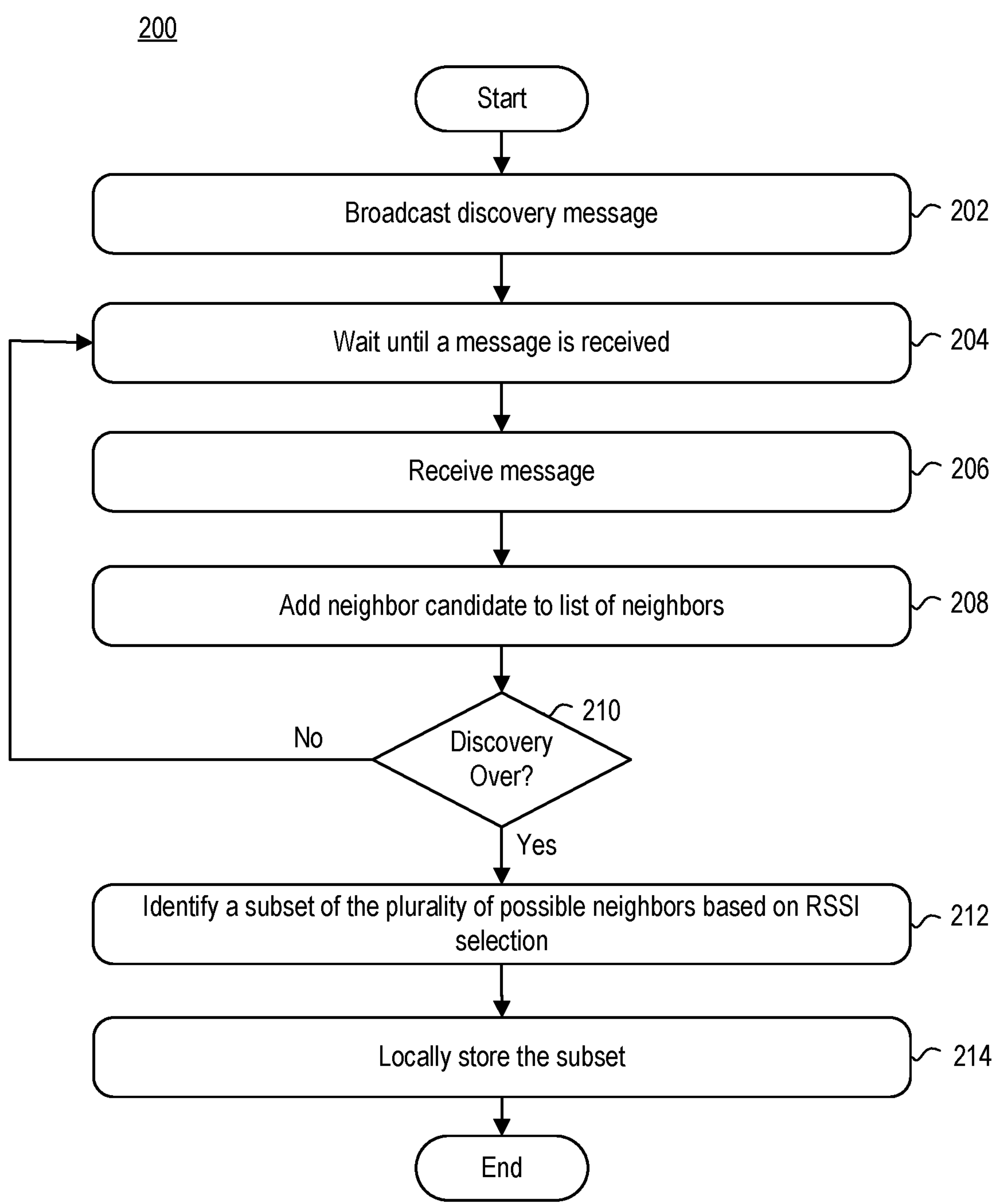
FIG. 2 is a flow diagram illustrating a method of identifying neighboring devices, according to example embodiments.

FIG. 2 is a flow diagram illustrating a method 200 of identifying neighboring devices, according to example embodiments. Method 200 may begin at step 202.

At step 202, a user device 102 may broadcast a discovery message. For example, user device 102-1 may generate a neighbor discovery packet to be transmitted via the transceiver of microcontroller 104-1. In some embodiments, the neighbor discovery packet may include a unique identifier corresponding to user device 102-1. In some embodiments, the neighbor discovery packet may further include a local time associated with user device 102-1 as determined by real-time clock 106. In some embodiments, user device 102 may broadcast multiple discovery messages. For example, user device 102 may broadcast multiple discovery messages at fixed time intervals to prevent clock drifting.

At step 204, user device 102 may wait until the discovery message is received. In some embodiments, user device 102-1 may send multiple discovery messages with the intent that the multiple discovery messages are received by a plurality of user device 102 within the ad-hoc network.

At step 206, user device 102 may receive a message from another sending user device. For example, user device 102-1 may receive a return message from user device 102-2, responsive to user device 102-2 receiving the discovery message. In some embodiments, upon receiving the return message from user device 102-2, user device 102-1 may generate an RSSI of the received message. The RSSI may indicate a signal strength of the return message originating form user device 102-2, thus providing an indication of how far user device 102-2 is from user device 102-1. In some embodiments, the return message may also include a local time associated with the sending user device. For example, the return message may include a local time associated with user device 102-2 as determined by real-time clock 106-2.

At step 208, user device 102-1 may add user device 102-2 to a list of neighbor candidates. In some embodiments, the list of neighbor candidates may be representative of all user devices 102 that received the discovery message from user device 102-1 and replied accordingly. In some embodiments, the list of neighbor candidates may include a device identifier corresponding to its user device, an RSSI, and a local time.

At step 210, user device 102 may determine whether the discovery process is over. In some embodiments, the discovery process may run for a fixed period. If, for example, at step 210, user device 102 determines that not all discovery messages have received a reply message or a time period for reply has not expired, then method 200 may revert to step 204, and user device 102 may continue to wait for messages. If, however, at step 210, user device 102 determines that all discovery messages have received a reply message or a time period for reply has expired, then method 200 may proceed to step 212.

At step 212, user device 102 may identify a subset of the plurality of neighbor candidates based on their RSSIs. For example, user device 102 may establish a neighbor list by filtering out those user devices that have a RSSI below a threshold value. In other words, user device 102-1 may select, as neighbors, those user devices 102 that may facilitate a maximum reach of a transmission.

At step 214, user device 102 may locally the established neighbor list. For example, once the neighbor candidates are filtered based on the RSSIs, user device 102 may locally save the neighbor list for subsequent sending or relaying of messages within the ad-hoc network.

Figure 3A:
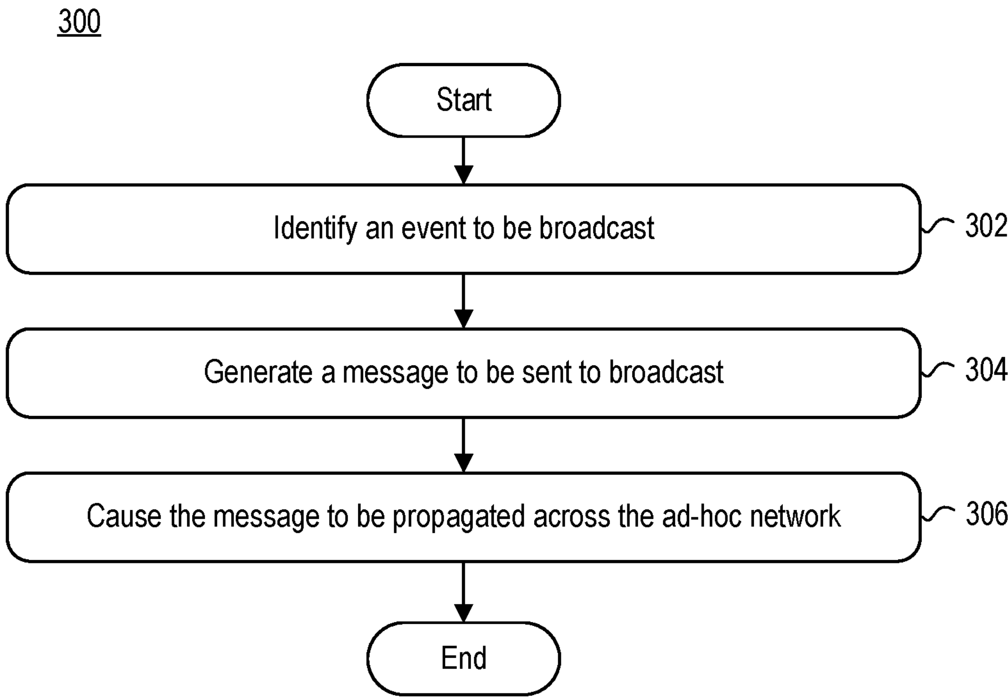
FIG. 3A is a flow diagram illustrating a method of sending a message to neighboring devices, according to example embodiments.

FIG. 3A is a flow diagram illustrating a method 300 of sending a message to neighboring devices, according to example embodiments. Method 300 may begin at step 302.

At step 302, user device 102-1 may identify an event to be broadcast. In some embodiments, the event may be a fall event detected by user device 102-1. In some embodiments, the event may be an insufficient vital event as detected by user device 102-1. In some embodiments, the event may be a geofence event as detected by user device 102-1. In some embodiments, the event may be a message generated by user device 102-1, such as an emergency event intended to be pushed from a care provider's device to all patient devices.

At step 304, user device 102-1 may generate a message to be propagated across the ad-hoc network. For example, microcontroller 104-2 may generate a data packet that includes a header, neighbor information, and content. The header may include a unique identifier corresponding to user device 102-1. In some embodiments, the header may also include a unique identifier or unique identifiers corresponding to intended recipients, i.e., neighbors on the stored neighbor list. In some embodiments, the header may not include any intended recipient. In such embodiments, the message may be configured to propagate through the network until every device in the network has received the message. In some embodiments, the header may also include a unique identifier that uniquely identifies the message. Neighbor information may include information associated with neighbors on the neighbor list of user device 102-1. For example, neighbor information may include a list of unique identifiers corresponding to neighboring user devices 102. In some embodiments, content may include an indication of the event to be broadcast.

At step 306, user device 102-1 may cause the message to be propagated across the ad-hoc network. For example, microcontroller 104-1 may broadcast the message using its radio transceiver to all devices within communicative range.

Figure 3B:
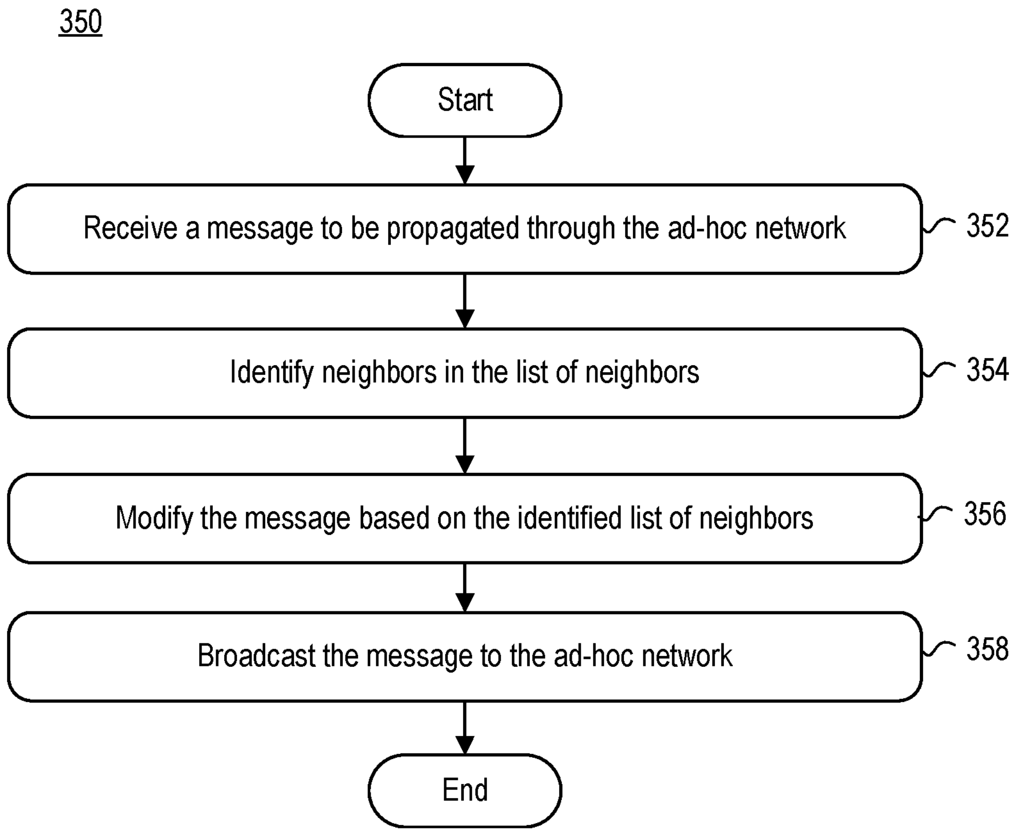
FIG. 3B is a flow diagram illustrating a method of relaying a message to neighboring devices, according to example embodiments.

FIG. 3B is a flow diagram illustrating a method 350 of relaying a message to neighboring devices, according to example embodiments. Method 350 may begin at step 352.

At step 352, user device 102 may receive a message to be propagated within an ad-hoc network. In some embodiments, the message may be received via a transceiver of microcontroller 104. Generally, the message may include at least a header, a neighbor list, and content. The header may indicate a sender or originator of the message. In some embodiments, the header may indicate the intended recipient of the message. In some embodiments, the header may not include any intended recipient. The neighbor list may include a list of user device identifiers corresponding to the neighbor list of the sender or originator of the message, as well as a list of user device identifiers corresponding to the neighbor lists of any intermediary devices between the sender or originator device and the receiving device.

At step 354, user device 102 may identify a list of neighbors to whom the message will be forwarded. For example, user device 102 may compare the neighbor list of neighbors within the message to the locally stored list of messages to identify the list of neighbors in its locally store neighbor list that have yet to receive the message. In this manner, user device 102 may ensure that the message is not transmitted once more to devices that already received the message.

At step 356, user device 102 may modify the message based on the identified list of neighbors. For example, to continue maintaining that the message is not subsequently re-sent to other user devices, user device 102 may append its identified list of neighbors to the list of neighbors in the message.

At step 358, user device 102 may broadcast the message to the ad-hoc network. For example, microcontroller 104 may broadcast the message using its radio transceiver to all devices within communicative range.

In some embodiments, user device 102 may locally store the identifier that uniquely identifies the message. For example, to ensure that there is not an endless loop of the same message being propagated throughout the network, user device 102 may store the identifier uniquely identifying the message locally. In this manner, should user device 102 mistakenly receive the message a second time, user device 102 can determine that it already received the message and can end the message loop.

First Example

Assume that Patient A has fallen within health care facility 100. As described across U.S. patent application Ser. No. 15/891,107, U.S. patent application Ser. No. 13/896,306, U.S. patent application Ser. No. 14/057,687, and U.S. patent application Ser. No. 13/057,676, which are hereby incorporated by reference in their entries, the fall may be detected by the user's wearable device. In some embodiments, the message broadcasting the fall may be sent along the ad-hoc network described above. Accordingly, the wearable device worn by Patient A (e.g., user device 102) may generate a message to be broadcast to its neighbor devices. The message may include a device identifier that uniquely identifies Patient A's wearable device, a list of neighboring devices, and an indication that a fall was detected. In some embodiments, the message may further include a unique identifier that uniquely identifies the message. Patient A's wearable device may then broadcast the message to its neighboring devices.

Second Example

Assume that Patient A has fallen within health care facility 100. As described across U.S. patent application Ser. No. 15/891,107, U.S. patent application Ser. No. 13/896,306, U.S. patent application Ser. No. 14/057,687, and U.S. patent application Ser. No. 13/057,676, which are hereby incorporated by reference in their entries, Patient A's wearable device may determine that a critical vital of Patient A has fallen below a threshold. In some embodiments, a message broadcasting the critical vital may be sent along the ad-hoc network described above. Accordingly, the wearable device worn by Patient A (e.g., user device 102) may generate a message to be broadcast to its neighbor devices. The message may include a device identifier that uniquely identifies Patient A's wearable device, a list of neighboring devices, and an indication that a critical vital was detected. Because the information is sensitive in nature, the content of the message may be encrypted to ensure that the contents are not leaked. In some embodiments, the message may further include a unique identifier that uniquely identifies the message. Patient A's wearable device may then broadcast the message to its neighboring devices.

Third Example

Assume that Patient A has fallen within health care facility 100. As described across U.S. patent application Ser. No. 15/891,107, U.S. patent application Ser. No. 13/896,306, U.S. patent application Ser. No. 14/057,687, and U.S. patent application Ser. No. 13/057,676, which are hereby incorporated by reference in their entries, Patient A's wearable device may determine that the Patient A has gone outside a geofenced area. In some embodiments, a message broadcasting the geofence event may be sent along the ad-hoc network described above. Accordingly, the wearable device worn by Patient A (e.g., user device 102) may generate a message to be broadcast to its neighbor devices. The message may include a device identifier that uniquely identifies Patient A's wearable device, a list of neighboring devices, and an indication that Patient A has gone beyond a geofenced area. In some embodiments, the message may further include a unique identifier that uniquely identifies the message. Patient A's wearable device may then broadcast the message to its neighboring devices.

Figures 4A, 4B:
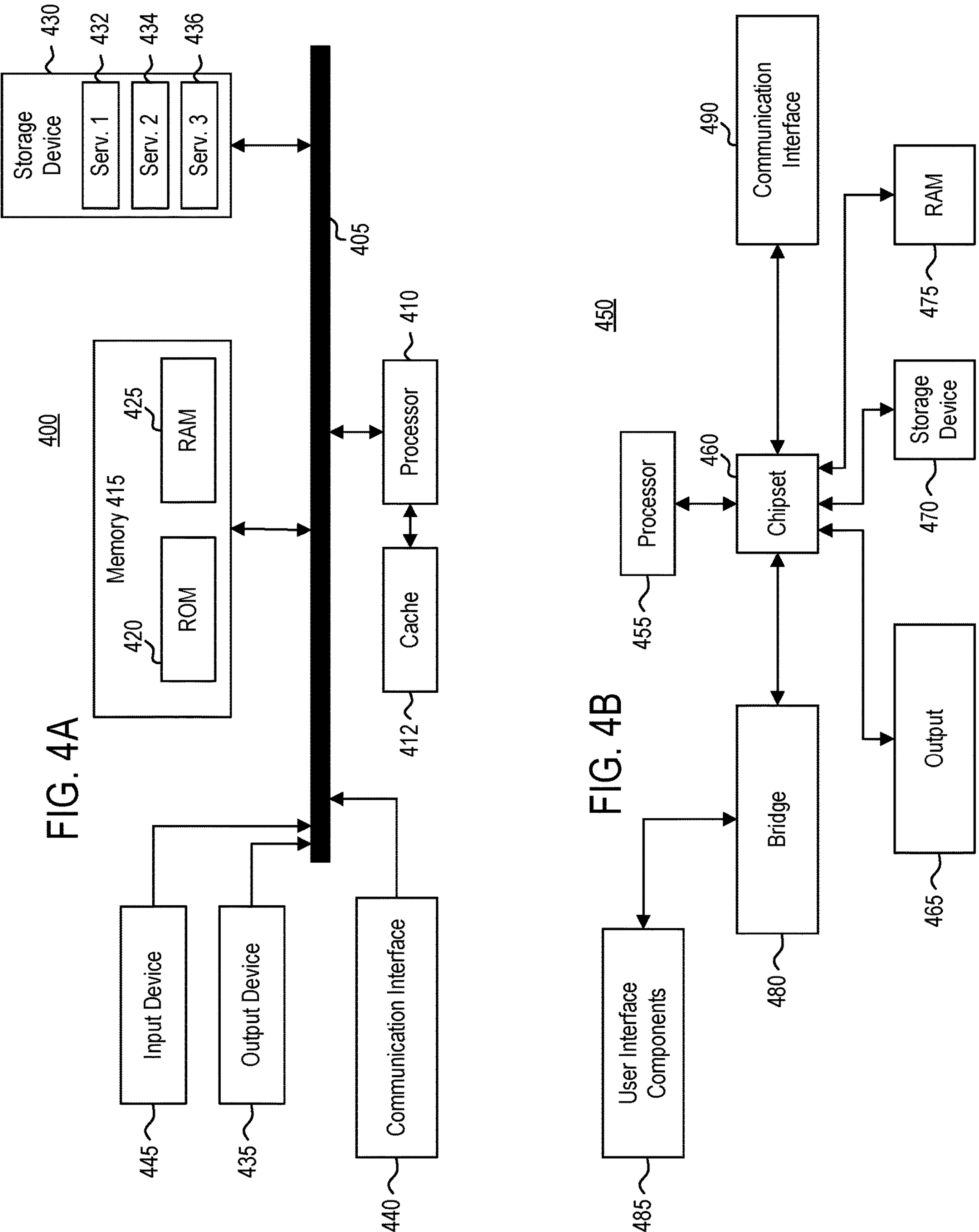
FIG. 4A is a block diagram illustrating a computing device, according to example embodiments of the present disclosure.
FIG. 4B is a block diagram illustrating a computing device, according to example embodiments of the present disclosure.

FIG. 4A illustrates a system bus architecture of computing system 400, according to example embodiments. System 400 may be representative of at least user device 102. One or more components of system 400 may be in electrical communication with each other using a bus 405. System 400 may include a processing unit (CPU or processor) 410 and a system bus 405 that couples various system components including the system memory 415, such as read only memory (ROM) 420 and random-access memory (RAM) 425, to processor 410.

System 400 may include a cache of high-speed memory connected directly with, in close proximity to, or integrated as part of processor 410. System 400 may copy data from memory 415 and/or storage device 430 to cache 412 for quick access by processor 410. In this way, cache 412 may provide a performance boost that avoids processor 410 delays while waiting for data. These and other modules may control or be configured to control processor 410 to perform various actions. Other system memory 415 may be available for use as well. Memory 415 may include multiple different types of memory with different performance characteristics. Processor 410 may include any general-purpose processor and a hardware module or software module, such as service 1 432, service 2 434, and service 3 436 stored in storage device 430, configured to control processor 410 as well as a special-purpose processor where software instructions are incorporated into the actual processor design. Processor 410 may essentially be a completely self-contained computing system, containing multiple cores or processors, a bus, memory controller, cache, etc. A multi-core processor may be symmetric or asymmetric.

To enable user interaction with the computing system 400, an input device 445 may represent any number of input mechanisms, such as a microphone for speech, a touch-sensitive screen for gesture or graphical input, keyboard, mouse, motion input, speech and so forth. An output device 435 may also be one or more of a number of output mechanisms known to those of skill in the art. In some instances, multimodal systems may enable a user to provide multiple types of input to communicate with computing system 400. Communications interface 440 may generally govern and manage the user input and system output. There is no restriction on operating on any particular hardware arrangement and therefore the basic features here may easily be substituted for improved hardware or firmware arrangements as they are developed.

Storage device 430 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 425, read only memory (ROM) 420, and hybrids thereof.

Storage device 430 may include services 432, 434, and 436 for controlling the processor 410. Other hardware or software modules are contemplated. Storage device 430 may be connected to system bus 405. In one aspect, a hardware module that performs a particular function may include the software component stored in a computer-readable medium in connection with the necessary hardware components, such as processor 410, bus 405, output device 435 (e.g., display), and so forth, to carry out the function.

FIG. 4B illustrates a computer system 450 having a chipset architecture that may represent user device 102. Computer system 450 may be an example of computer hardware, software, and firmware that may be used to implement the disclosed technology. System 450 may include a processor 455, representative of any number of physically and/or logically distinct resources capable of executing software, firmware, and hardware configured to perform identified computations. Processor 455 may communicate with a chipset 460 that may control input to and output from processor 455.

In this example, chipset 460 outputs information to output 465, such as a display, and may read and write information to storage device 470, which may include magnetic media, and solid-state media, for example. Chipset 460 may also read data from and write data to storage device 475 (e.g., RAM). A bridge 480 for interfacing with a variety of user interface components 485 may be provided for interfacing with chipset 460. Such user interface components 485 may include a keyboard, a microphone, touch detection and processing circuitry, a pointing device, such as a mouse, and so on. In general, inputs to system 450 may come from any of a variety of sources, machine generated and/or human generated.

Chipset 460 may also interface with one or more communication interfaces 490 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 455 analyzing data stored in storage device 470 or storage device 475. Further, the machine may receive inputs from a user through user interface components 485 and execute appropriate functions, such as browsing functions by interpreting these inputs using processor 455.

It may be appreciated that example systems 400 and 450 may have more than one processor 410 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and may be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

The invention claimed is:

1. A method of transmitting an emergency notification among patients in a health care facility, comprising:

establishing, by a first patient device, an ad-hoc network of devices within the health care facility, the ad-hoc network of devices comprising a plurality of other patient devices and a plurality of health care provider devices;

detecting, by the first patient device, a trigger event for sending a message across the ad-hoc network;

responsive to the detecting, generating, by the first patient device, the message comprising a header comprising a unique identifier corresponding to the first patient device, a locally stored list of neighboring devices to the first patient device, and an indication of the trigger event;

causing, by the first patient device, the message to propagate across the ad-hoc network by broadcasting the message via a radio transceiver of the first patient device;

receiving, by a second patient device, the message broadcast by the first patient device;

comparing, by the second patient device, the list of neighboring devices in the message to a second list of neighboring devices stored local to the second patient device;

based on the comparing, identifying, by the second patient device, a third list of neighboring devices unique to the second list of neighboring devices;

appending, by the second patient device, the third list of neighboring devices to the list of neighboring devices in the message; and causing, by the second patient device, the message to continue to propagate across the ad-hoc network by broadcasting the message via a second radio transceiver of the second patient device, the message including the third list of neighboring devices and the list of neighboring devices.

2. The method of claim 1, wherein establishing, by the first patient device, the ad-hoc network of devices within the health care facility comprises:

initiating a discovery process, the discovery process comprising:

broadcasting a discovery message to be received by the plurality of other patient devices;

receiving a plurality of reply messages from at least a subset of the plurality of other patient devices;

determining a signal strength corresponding to each reply message; and generating the locally stored list of neighboring devices based on the signal strength of each reply message.

3. The method of claim 2, wherein each reply message of the plurality of reply messages comprises a local time corresponding to the other patient device that sent the reply message.

4. The method of claim 3, wherein the discovery process further comprises:

synchronizing a first local clock of the first patient device based on each local time of each other patient device in the list of neighboring devices.

5. The method of claim 1, wherein the message further comprises an identifier uniquely identifying the message.

6. The method of claim 5, further comprising:

comparing, by the second patient device, the identifier uniquely identifying the message to a list of locally stored message identifiers; and determining, by the second patient device, that the second patient device has not received the message based on the comparing.

7. A health care system for a health care facility comprising:

a first patient device comprising:

a processor; and a memory having programming instructions stored thereon, which, when executed by the processor, cause the first patient device to perform operations comprising:

establishing, by the first patient device, an ad-hoc network of devices within the health care facility, the ad-hoc network of devices comprising a plurality of other patient devices and a plurality of health care provider devices;

detecting, by the first patient device, a trigger event for sending a message across the ad-hoc network;

responsive to the detecting, generating, by the first patient device, the message comprising a header comprising a unique identifier corresponding to the first patient device, a locally stored list of neighboring devices to the first patient device, and an indication of the trigger event; and causing, by the first patient device, the message to propagate across the ad-hoc network by broadcasting the message via a radio transceiver of the first patient device; and a second patient device comprising:

a second processor; and a second memory having second programming instructions stored thereon, which, when executed by the second processor, cause the second patient device to perform further operations comprising:

receiving, by the second patient device, the message broadcast by the first patient device;

comparing, by the second patient device, the list of neighboring devices in the message to a second list of neighboring devices stored local to the second patient device;

based on the comparing, identifying, by the second patient device, a third list of neighboring devices unique to the second list of neighboring devices;

appending, by the second patient device, the third list of neighboring devices to the list of neighboring devices in the message; and causing, by the second patient device, the message to continue to propagate across the ad-hoc network by broadcasting the message via a second radio transceiver of the second patient device.

8. The health care system of claim 7, wherein establishing, by the first patient device, the ad-hoc network of devices within the health care facility comprises:

initiating a discovery process, the discovery process comprising:

broadcasting a discovery message to be received by the plurality of other patient devices;

receiving a plurality of reply messages from at least a subset of the plurality of other patient devices;

determining a signal strength corresponding to each reply message; and generating the locally stored list of neighboring devices based on the signal strength of each reply message.

9. The health care system of claim 8, wherein each reply message of the plurality of reply messages comprises a local time corresponding to the other patient device that sent the reply message.

10. The health care system of claim 9, wherein the discovery process further comprises:

synchronizing a first local clock of the first patient device based on each local time of each other patient device in the list of neighboring devices.

11. The health care system of claim 7, wherein the message further comprises an identifier uniquely identifying the message.

12. The health care system of claim 11, wherein the further operations further comprise:

comparing, by the second patient device, the identifier uniquely identifying the message to a list of locally stored message identifiers; and determining, by the second patient device, that the second patient device has not received the message based on the comparing.

13. A non-transitory computer readable medium comprising one or more sequences of instructions, which, when executed by a processor, causes one or more of a first patient device or a second patient device to perform operations, comprising:

establishing, by the first patient device, an ad-hoc network of devices within a health care facility, the ad-hoc network of devices comprising a plurality of other patient devices and a plurality of health care provider devices;

detecting, by the first patient device, a trigger event for sending a message across the ad-hoc network;

responsive to the detecting, generating, by the first patient device, the message comprising a header comprising a unique identifier corresponding to the first patient device, a locally stored list of neighboring devices to the first patient device, and an indication of the trigger event;

causing, by the first patient device, the message to propagate across the ad-hoc network by broadcasting the message via a radio transceiver of the first patient device;

receiving, by a second patient device, the message broadcast by the first patient device;

comparing, by the second patient device, the list of neighboring devices in the message to a second list of neighboring devices stored local to the second patient device;

based on the comparing, identifying, by the second patient device, a third list of neighboring devices unique to the second list of neighboring devices;

appending, by the second patient device, the third list of neighboring devices to the list of neighboring devices in the message; and causing, by the second patient device, the message to continue to propagate across the ad-hoc network by broadcasting the message via a second radio transceiver of the second patient device, the message including the third list of neighboring devices and the list of neighboring devices.

14. The non-transitory computer readable medium of claim 13, wherein establishing, by the first patient device, the ad-hoc network of devices within the health care facility comprises:

initiating a discovery process, the discovery process comprising:

broadcasting a discovery message to be received by the plurality of other patient devices;

receiving a plurality of reply messages from at least a subset of the plurality of other patient devices;

determining a signal strength corresponding to each reply message; and generating the locally stored list of neighboring devices based on the signal strength of each reply message.

15. The non-transitory computer readable medium of claim 14, wherein each reply message of the plurality of reply messages comprises a local time corresponding to the other patient device that sent the reply message.

16. The non-transitory computer readable medium of claim 15, wherein the discovery process further comprises:

synchronizing a first local clock of the first patient device based on each local time of each other patient device in the list of neighboring devices.

17. The non-transitory computer readable medium of claim 13, further comprising:

maintaining, by the first patient device, a message list comprising message identifiers of previously received messages in the ad-hoc network.

18. The non-transitory computer readable medium of claim 17, further comprising:

receiving, by the first patient device, a second message broadcast to the ad-hoc network;

identifying, by the first patient device, a message identifier corresponding to the second message;

comparing, by the first patient device, the message identifier to the message list;

determining, by the first patient device, that the second message has already been received; and causing, by the first patient device, the second message to stop propagating in the ad-hoc network.

* * * * *